(12) United States Patent
Levin et al.

(10) Patent No.: US 9,375,524 B2
(45) Date of Patent: Jun. 28, 2016

(54) METHOD AND ARRANGEMENT FOR VENTING GASES FROM A CONTAINER HAVING A POWDERED CONCENTRATE FOR USE IN HEMODIALYSIS

(75) Inventors: Roland Levin, San Ramon, CA (US); Christian Schlaeper, Wehrheim (DE); Martin Crnkovich, Walnut Creek, CA (US); Harald Peter, Schweinfurt (DE)

(73) Assignees: Fresenius Medical Care Holdings, Inc., Waltham, MA (US); Fresenius Medical Care Deutschland GmbH (DE)

( * ) Notice: Subject to any disclaimer, the term of this patent is extended or adjusted under 35 U.S.C. 154(b) by 724 days.

(21) Appl. No.: 13/153,140

(22) Filed: Jun. 3, 2011

(65) Prior Publication Data

US 2012/0305485 A1    Dec. 6, 2012

(51) Int. Cl.
| | |
|---|---|
| *B01D 61/30* | (2006.01) |
| *B01D 61/32* | (2006.01) |
| *B01D 19/00* | (2006.01) |
| *B01D 61/26* | (2006.01) |
| *A61M 1/16* | (2006.01) |

(52) U.S. Cl.
CPC ............. *A61M 1/1658* (2013.01); *A61M 1/167* (2014.02); *A61M 1/1666* (2014.02)

(58) Field of Classification Search
CPC ............ A61M 1/1656; A61M 1/1658; A61M 2205/3331; A61M 1/3626; A61M 1/3627; A61M 1/167; A61M 1/1666
USPC .......... 210/644, 645, 646, 739, 746, 750, 85, 210/97, 109, 110, 120, 137, 143, 188, 218, 210/252, 257.1, 258, 436, 472; 604/403, 604/405, 408

See application file for complete search history.

(56) References Cited

U.S. PATENT DOCUMENTS

| | | |
|---|---|---|
| 3,887,499 A | 6/1975 | Hodgdon, Jr. |
| 3,982,538 A | 9/1976 | Sharpe |
| 3,985,135 A | 10/1976 | Carpenter et al. |
| 4,026,669 A | 5/1977 | Leonard et al. |
| 4,137,160 A | 1/1979 | Ebling et al. |
| 4,370,983 A | 2/1983 | Lichtenstein |
| 4,459,139 A | 7/1984 | vonReis et al. |
| 4,488,961 A | 12/1984 | Spencer |
| 4,507,119 A | 3/1985 | Spencer |
| 4,530,759 A | 7/1985 | Schal |
| 4,590,227 A | 5/1986 | Nakamura et al. |
| 4,630,727 A | 12/1986 | Feriani et al. |
| 4,643,713 A | 2/1987 | Viitala |

(Continued)

FOREIGN PATENT DOCUMENTS

| | | |
|---|---|---|
| CN | 101687070 A | 3/2010 |
| CN | 101711171 A | 5/2010 |

(Continued)

OTHER PUBLICATIONS

PCT/US2012/040202 International Search Report (Aug. 22, 2012).

(Continued)

*Primary Examiner* — John Kim
(74) *Attorney, Agent, or Firm* — Leydig, Voit & Mayer, Ltd.

(57) ABSTRACT

An arrangement and a method for venting gases from a container containing mixture of salt concentrate and fluid for use in dialysis, including venting the gases to a hydrochamber disposed upstream of the container.

18 Claims, 3 Drawing Sheets

(56) References Cited

U.S. PATENT DOCUMENTS

| | | |
|---|---|---|
| 4,684,460 A | 8/1987 | Issautier |
| 4,713,171 A | 12/1987 | Polaschegg |
| 4,728,006 A | 3/1988 | Drobish et al. |
| 4,770,769 A | 9/1988 | Schael |
| 4,784,495 A | 11/1988 | Jonsson et al. |
| 5,061,236 A | 10/1991 | Sutherland et al. |
| 5,330,425 A | 7/1994 | Utterberg |
| 5,385,564 A | 1/1995 | Slater et al. |
| 5,441,636 A | 8/1995 | Chevallet et al. |
| 5,460,446 A | 10/1995 | Chevallet et al. |
| 5,498,338 A | 3/1996 | Kruger et al. |
| 5,511,875 A | 4/1996 | Jönsson et al. |
| 5,540,265 A | 7/1996 | Polaschegg et al. |
| 5,578,070 A | 11/1996 | Utterberg |
| 5,614,677 A | 3/1997 | Wamsiedler et al. |
| 5,616,305 A | 4/1997 | Mathieu |
| 5,628,908 A | 5/1997 | Kamen et al. |
| 5,643,205 A | 7/1997 | Utterberg |
| 5,711,883 A | 1/1998 | Folden et al. |
| 5,727,877 A | 3/1998 | Chevallet et al. |
| 5,731,365 A | 3/1998 | Engelhardt et al. |
| 5,989,423 A | 11/1999 | Kamen et al. |
| 6,062,436 A | 5/2000 | Fuchs |
| 6,179,801 B1 | 1/2001 | Holmes et al. |
| 6,196,987 B1 | 3/2001 | Holmes et al. |
| 6,200,287 B1 | 3/2001 | Keller et al. |
| 6,231,537 B1 | 5/2001 | Holmes et al. |
| 6,234,989 B1 | 5/2001 | Brierton et al. |
| 6,280,406 B1 | 8/2001 | Dolecek et al. |
| 6,336,916 B1 | 1/2002 | Bormann et al. |
| 6,337,049 B1 | 1/2002 | Tamari |
| 6,361,518 B1 | 3/2002 | Brierton et al. |
| 6,383,158 B1 | 5/2002 | Utterberg et al. |
| 6,409,696 B1 | 6/2002 | Toavs et al. |
| 6,497,674 B1 | 12/2002 | Steele et al. |
| 6,514,225 B1 | 2/2003 | Utterberg et al. |
| 6,536,278 B1 | 3/2003 | Scagliarini |
| 6,725,726 B1 | 4/2004 | Adolfs et al. |
| 6,730,055 B2 | 5/2004 | Bainbridge et al. |
| 6,755,801 B2 | 6/2004 | Utterberg et al. |
| 6,764,460 B2 | 7/2004 | Dolecek et al. |
| 6,790,195 B2 | 9/2004 | Steele et al. |
| 6,852,090 B2 | 2/2005 | Burbank et al. |
| 6,887,214 B1 | 5/2005 | Levin et al. |
| 7,021,148 B2 | 4/2006 | Kuhn et al. |
| 7,115,107 B2 | 10/2006 | Delnevo et al. |
| 7,223,262 B2 | 5/2007 | Brehm et al. |
| 7,275,665 B2 | 10/2007 | Young |
| 7,603,907 B2 | 10/2009 | Reiter et al. |
| 7,621,983 B2 | 11/2009 | Neri |
| 2002/0039994 A1 | 4/2002 | Scherhag et al. |
| 2002/0072718 A1 | 6/2002 | Brugger et al. |
| 2002/0179527 A1 | 12/2002 | Yao |
| 2004/0019312 A1 | 1/2004 | Childers et al. |
| 2004/0052689 A1 | 3/2004 | Yao |
| 2005/0054968 A1 | 3/2005 | Giannella |
| 2005/0230292 A1 | 10/2005 | Beden et al. |
| 2007/0086924 A1 | 4/2007 | Moses |
| 2007/0193940 A1 | 8/2007 | Duchamp et al. |
| 2007/0269340 A1 | 11/2007 | Dannenmaier et al. |
| 2010/0133189 A1 | 6/2010 | Maierhofer et al. |
| 2010/0292627 A1 | 11/2010 | Caleffi et al. |
| 2011/0120302 A1 | 5/2011 | Raiford et al. |
| 2011/0120946 A1 | 5/2011 | Levin et al. |

FOREIGN PATENT DOCUMENTS

| | | |
|---|---|---|
| DE | 41 13 032 A1 | 11/1991 |
| DE | 103 13 965 B3 | 10/2004 |
| DE | 102005001779 A1 | 9/2006 |
| EP | 0 270 100 A2 | 6/1988 |
| EP | 0 278 100 A2 | 8/1988 |
| EP | 0 327 136 A2 | 8/1989 |
| EP | 0 714 668 A1 | 6/1996 |
| EP | 0 728 509 A2 | 8/1996 |
| EP | 1 529 545 A2 | 5/2005 |
| EP | 1 547 630 A1 | 6/2005 |
| EP | 1 728 526 A1 | 12/2006 |
| EP | 1 454 643 B1 | 3/2008 |
| EP | 1 894 587 A1 | 3/2008 |
| EP | 2 226 087 A1 | 9/2010 |
| WO | WO 01/50949 A1 | 7/2001 |
| WO | WO 2007/050211 A2 | 5/2007 |
| WO | WO 2008/002370 A2 | 1/2008 |
| WO | WO 2008/065470 A1 | 6/2008 |

OTHER PUBLICATIONS

Manns, Markus et al., "The Acu-Men: A New Device for Continuous Renal Replacement Therapy in Acute Renal Failure," *Kidney International*, 54, 268-274 (1998).

European Patent Application No. 12 79 3888 Search Report (Oct. 7, 2014).

Chinese Patent Application No. 201280027135.6, Search Report (Feb. 28, 2015).

METHOD AND ARRANGEMENT FOR VENTING GASES FROM A CONTAINER HAVING A POWDERED CONCENTRATE FOR USE IN HEMODIALYSIS

BACKGROUND OF THE INVENTION

Dialysis is performed as a treatment for patients suffering from renal insufficiency. Dialysis can be performed either in the peritoneum, or through extracorporeal dialysis involving filtration of blood. These two dialysis methods have in common the fact that dialysis fluids or dialysates take up the degradation products of metabolism. These dialysates usually contain high levels of sodium chloride and other electrolytes, such as calcium chloride, or potassium chloride, a buffer substance, such as bicarbonate, or acetate and acid to establish a physiological pH, plus optionally, glucose or another osmotic agent.

Dialysates are either supplied as ready-to-use solutions or they are prepared on site from concentrates, including solid concentrates. Solids offer the advantage of a small package volume and a low weight. Although solids also have disadvantages—electrolyte salts, for example, are highly hygroscopic—there is a trend toward offering only solid components for preparation of dialysates.

In the above mentioned hemodialysis systems, a flexible bag or container filled with a powdered salt concentrate is used to generate a concentrated salt solution. Purified fluid is added to the top of the container and the concentrated solution is removed from the bottom of the container. When the concentrated solution is removed from the bottom of the bag it is generally delivered to the hemodialysis machine for use in the dialysate. It is important that the fluid level in the container with the salt concentrate is maintained above the level of the salt in the container, when the solution is being pumped out of the bottom of the container. Under normal operation, the fluid level above the powdered salt layer is maintained or increases as the salt concentrate is consumed. However, if the fluid level falls below the level of the salt concentrate, air or gases in the bag may be pumped through the salt concentrate and out of the bottom of the container into the dialysate.

During hemodialysis using systems such as described in U.S. Pat. No. 5,385,564 and U.S. Pat. No. 5,616,305, incorporated by reference herein, dry bicarbonate or acid concentrate is mixed with dialysate via a container using one or more ports. Even when the container is filled there is always air remaining in the container. The system cannot remove all of the air from the container without evacuating the air from the container via a vacuum system to create negative pressure, before filling the container with fluid.

To deter air from being drawn into the hydraulics of the machine during operation, it is desirable to fill the container with a sufficient volume or fluid to maintain a fluid layer above the dry powder. In some systems, without removing air from the bag via a vacuum, some containers will not maintain the correct fluid layer, and thus, extra air passes into the hydraulics which requires excessive venting procedures. The new method and arrangement of the present invention addresses the problem without the need to generate a vacuum to evacuate the gases from the concentrate.

BRIEF SUMMARY OF THE INVENTION

In an embodiment, the present invention provides a system and a method for venting gases from a container containing a mixture of salt concentrate and fluid for use with a dialysis apparatus. According to a disclosed method, the gases are vented to a hydrochamber disposed upstream of the container.

According to a disclosed method, the system includes a container having an inlet and at least one gas outlet having a gas outlet control valve and a hydrochamber upstream of the container, the method comprising the steps of opening the gas outlet control valve to vent gases from the container to the hydrochamber, the gas outlet control valve selectively fluidly coupling the container to the hydrochamber, and closing the gas outlet control valve when at least a portion of the gases contained within the container are vented from the container to the hydrochamber.

In another embodiment, the present invention also provides a system for use with a dialysis apparatus. The system comprises a container having an inlet and at least one gas outlet, and a hydrochamber disposed upstream of the container. The system further includes a first hydraulic line fluidly coupling the gas outlet of the container to the hydrochamber, and a gas outlet control valve disposed in said first hydraulic line to provide selective fluid flow through the first hydraulic line.

DETAILED DESCRIPTION OF THE INVENTION

Figure 1:
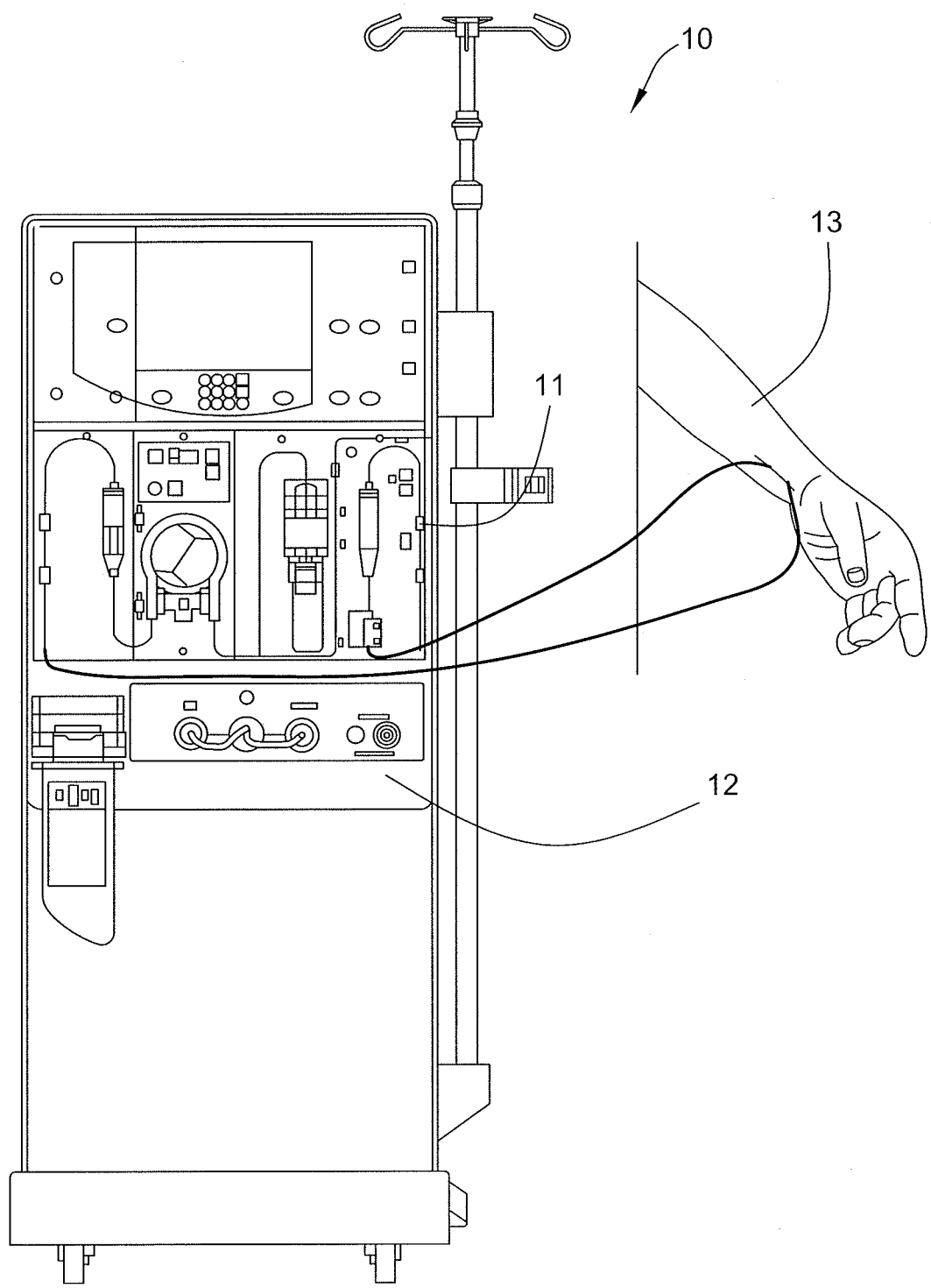
FIG. 1 is a schematic diagram the general environment where the system is operating. A patient is shown attached to a dialysis apparatus. It is understood that the system of the present invention supplies dialysate solution to such an apparatus for use in hemodialysis.

Turning now to the drawings, FIG. 1 displays the general context of a dialysis system 10. The dialysis system 10 includes the dialyzer 11, and a subsystem 12 for preparing a salt solution from a powdered salt concentrate. The salt solution is provided to the dialyzer 11 for administration to a patient 13. The dialysis system 10 may additionally include various other optional subsystems and equipment, which are not addressed in this disclosure in detail.

Figure 2:
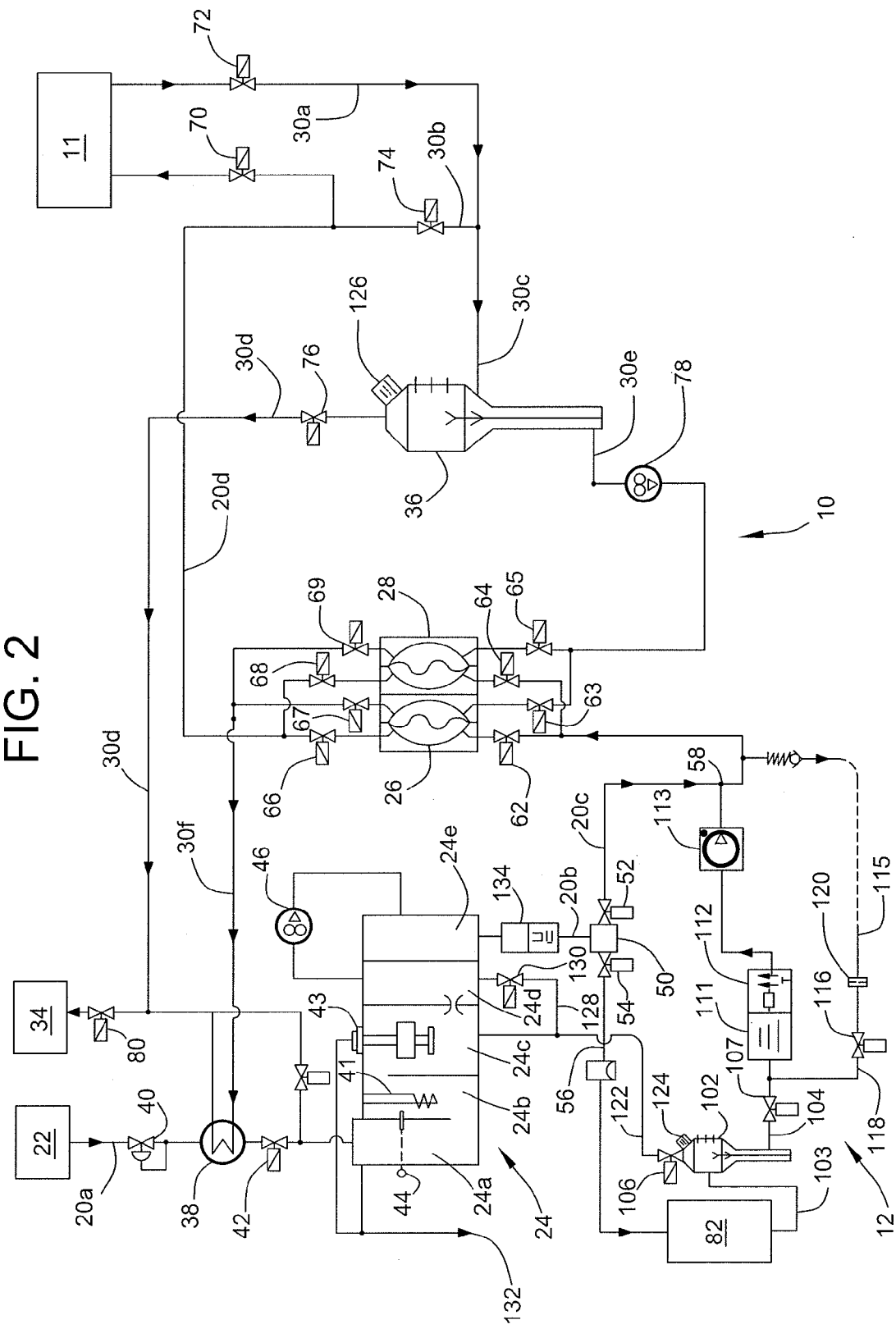
FIG. 2 is a schematic diagram of an embodiment of a system for the production and discharge of a liquid hemodialysis concentrate for use in a dialysis apparatus.

FIG. 2 illustrates a representative hydraulic arrangement of the dialysis system 10. By way of a general overview of the operation, the system 10 includes a main hydraulic line or mainline 20a-d (collectively referenced as 20) that is fluidly coupled to a fluid source 22 at one end, and to the dialyzer 11 at the other end, with various optional assemblies disposed along the mainline 20. It is noted that the mainline 20a-d may include a plurality of hydraulic lines. In the illustrated embodiment, optional assemblies are disposed along the mainline 20 in addition to the subsystem 12 for preparing a salt solution and may include a hydroblock 24 and one or more balancing chambers 26, 28.

A return line 30a-f (collectively referenced as 30) from the dialyzer 11 provides return flow from the dialyzer 11 to a drain 34. As with the mainline, the return line 30a-f may include a plurality of hydraulic lines. Subassemblies such as an air separation chamber 36 or a heat exchanger 38 may be provided along the return line 30. It is noted that not all elements of the illustrated hydraulic arrangement are necessary to the structure and operation of the subsystem 12 for preparing a salt solution from a powdered salt concentrate, although a general explanation is provided herein in the interest of completeness.

Turning now to the specifics of the illustrated hydraulic arrangement, the fluid source 22 may include any appropriate type of fluid or fluids. For example, a reverse osmosis fluid (RO fluid) source may be provided. It will be appreciated that an alternate fluid may be provided as required by the system 10. While the fluid referenced in this disclosure will be typically be purified water, it is intended that the terms "fluid" and "fluids" will encompass other appropriate fluids for the purposes of the disclosed method and arrangement.

Fluid from the fluid source 22 flows through mainline 20*a* to the hydroblock 24. In this embodiment, the heat exchanger 38, a pressure regulator 40, and a control valve 42 are provided along the mainline 20*a* between the fluid source 22 and the hydroblock 24. While the valve 42 controls overall flow to the mainline 20*a*, the pressure regulator 40 may control the pressure of the fluid as it passes through this section of the mainline 20*a*. The heat exchanger 38 may heat the fluid somewhat with heat from the return spent fluid, as will be discussed below.

In the embodiment illustrated, the hydroblock 24 is a multichambered unit (chambers 24*a*-24*e* being illustrated), the fluid being heated by a heater 41 in chamber 24*b* and vented to a vent 43 in chamber 24*c* as the fluid flows through the various chambers 24*a*-*e* of the hydroblock 24. The fluid temperature within the hydroblock 24 may be monitored and/or controlled by a control thermostat 44. A deaeration pump 46 pumps fluid between the forth and fifth chambers 24*d*, 24*e* of the hydroblock 24 to return the fluid to the mainline 20*b*.

Leaving the hydroblock 24, the mainline 20*b* bifurcates at a branch point 50. Valves 52, 54 control the flow of fluid to the continuing mainline 20*c* and a subsystem line 56, respectively. If the valve 54 is closed and valve 52 open, the fluid continues through the valve 52 to the mainline 20*c*. Conversely, if the valve 54 is open and the valve 52 closed, fluid proceeds through valve 54 to the subsystem line 56. As with all of the valves in this disclosure, the valves 52, 54 may be simple shut-off valves, or other multiposition valves. For example, valves 52, 54 may be replaced by a single valve that includes positions that arrest flow entirely, that direct flow to the subsystem line 56, or that direct flow along the mainline 20*c*.

The subsystem line 56 connects flow from the mainline 20*b* to the subsystem 12 for preparing a salt solution, as will be explained in greater detail below. After leaving the subsystem 12, the salt solution is returned to the mainline 20*c* at junction 58. The continuing mainline 20*c* directs flow to the balance chambers 26, 28, flow through the balancing chambers 26, 28 being controlled by a plurality of valves 62-69. Each of the balancing chambers 26, 28 includes two separate subchambers separated by a flexible membrane, the significance of which will be discussed below. Flow from the subsystem 12 flows into the respective balancing chambers 26, 28 through valves 62 and 64, and out from the balancing chambers 26, 28 through valves 66, 68.

Leaving the balancing chambers 26, 28, the solution is directed through mainline 20*d*. Flows to and from the dialyzer 11 are controlled by a pair of control valves 70, 72 disposed along the mainline 20*d* and the return line 30*a*, respectively, as well as a bypass valve 74 disposed in bypass line 30*b* between the mainline 20*d* and the return line 30*a*. Thus, fluid from the balancing chambers 26, 28 flowing through mainline 20*d* moves on to the dialyzer 11 when dialyzer inlet valve 70 is in the open configuration, and bypass valve 74 in the bypass line 30*b* is in the closed position.

Following usage in the dialyzer 11, spent fluid passes the control valve 72 to return to the system 10 through return line 30*a* and 30*c* with the bypass valve 74 is in the closed position. To ensure accurate operation of the balancing chambers 26, 28, as discussed below, spent fluid passes into the air separation chamber 36. From the air separation chamber 36, separated gases, and potentially fluid, are passed through return line 30*d* to the drain 34 by opening shutoff valves 76 and 80. Return fluid, from which the gases have been separated in the air separation chamber 36, may be pumped by flow pump 78 through return line 30*e* to one or both of the balance chambers 26, 28 through valves 63, 65. Leaving the balance chambers 26, 28 through valves 67, 69, respectively, the spent fluid is directed to a heat exchanger 38 and the drain 34 by way of return line 30*f*, overall flow to the drain 34 being controlled by shutoff valve 80. It will be appreciated that the heated spent fluid passing through the heat exchanger 38 may be used to heat the fluid flowing from the fluid source 22 to the hydroblock 24.

As used in this disclosure, the term "air separation chamber" is used to signify a structure that allows the separation and collection of gases from a solution, and permits the separate removal of each through respective outlets. Further, as used in this disclosure, the term "gas" or "gases" is not limited to air, but may include or exclude other gases, such as carbon dioxide, etc.

Operation of the balance chambers 26, 28 is known in the art. Within the balance chambers 26, 28, fresh fluid from the subsystem 12 passes along one side of the internal membranes, while spent fluid passes along the other side of the internal membranes. As will be appreciated by those of skill in the art, this pumping of spent fluid from line 30*e* along one side of the membrane with fresh fluid passing along the other side of the membrane results in a balanced provision of fluid from and to the dialyzer 11 during use.

Returning now to the structure and operation of the subsystem 12 for preparation of a salt solution, as explained above, fluid flowing from the mainline 20*b* from the hydroblock 24 may be directed to the subsystem 12 by opening the control valve 54 and closing control valve 52 at adjacent junction 50 to provide flow to the subsystem line 56. To prepare the salt solution, fluid from the subsystem line 56 enters a container 82, which contains a powdered salt concentrate. The container 82 may be of any appropriate design, and may include a collapsible, replaceable bag that encloses the powdered salt concentrate. As utilized in this disclosure, the term "container" 82 will be used to designate any or all of a rigid container, a semiflexible container, or a flexible container, such as a bag, such as it illustrated, for example, in U.S. Pat. No. 7,223,262.

Figure 3:
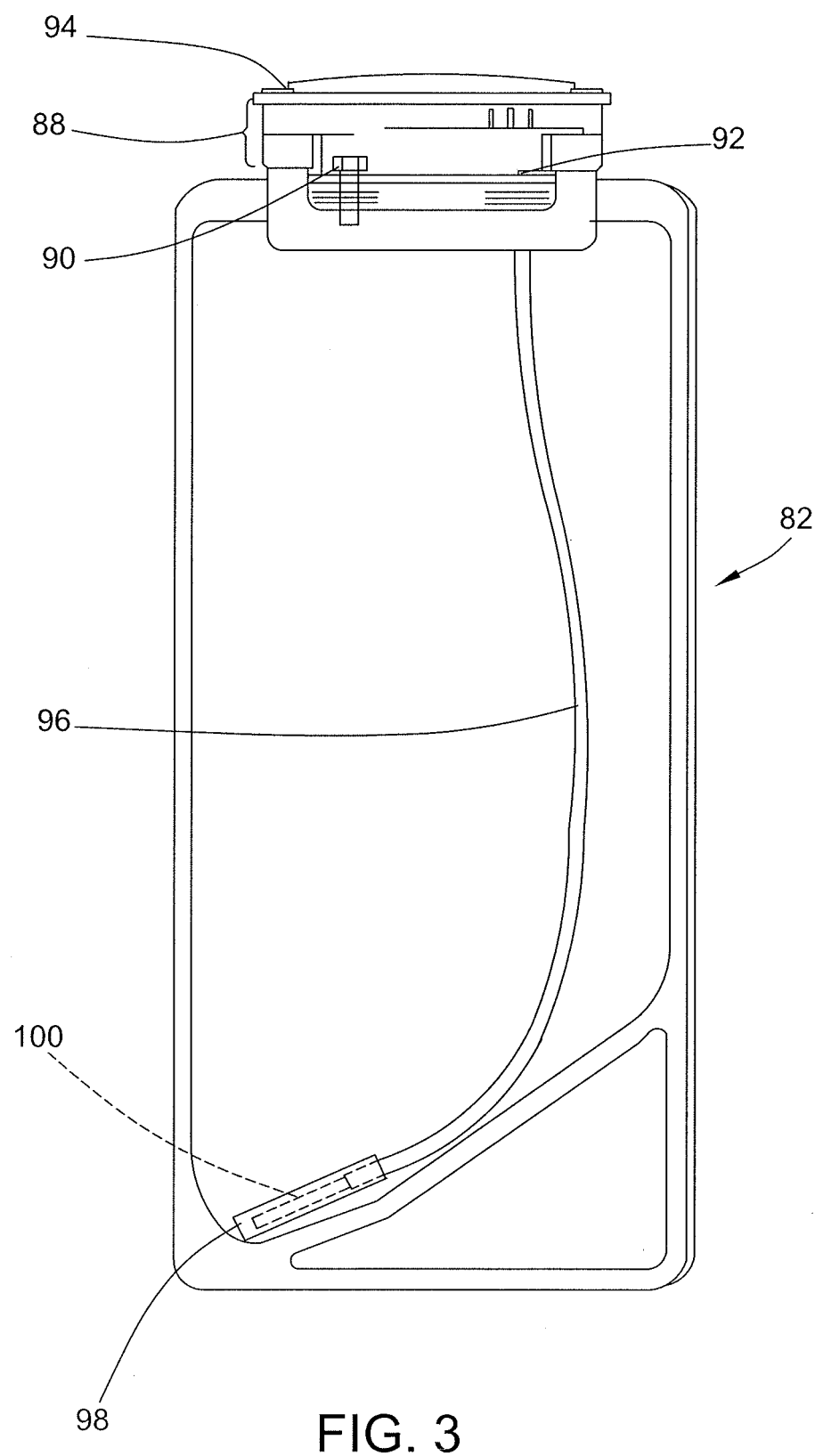
FIG. 3 is a representative partially cross-sectioned view of an embodiment of a container having a powdered salt concentrate that can be use in the method and system of the present invention.

An example of a container 82 in accordance with the disclosed method is shown in FIG. 3. In this partially cross-sectioned view, the container 82 includes a protective cover 94. The container 82 may be coupled to the subsystem 12 by any appropriate arrangement. In the illustrated embodiment, the container 82 is coupled to the subsystem 12 by a connector 88 having an inlet 90 and an outlet 92. Although the inlet 90 and outlet 92 are shown in an upper portion of the container 82, the inlet 90 and outlet 92 may be alternately disposed, so long as the requisite mixing is obtained as provided by the disclosed method. For example, the inlet may be disposed in a lower portion of the container 82 to allow the fluid to be injected upward into the container 82 to encourage agitation to facilitate mixing.

In order to allow the mixed salt solution to be withdrawn from a container 82 that is not completely full, the outlet 92 originates below the level of fluid in the container 82. In the illustrated embodiment, a tube 96 having a lower opening 98 is fluidly coupled to the outlet 92 such that the opening 98 may be disposed in a lower portion of the container 82, that is, below the fluid level. To inhibit the intake of powdered salt that is not yet dissolved, a filter 100 may be disposed at the opening 98. The filter 100 may be made of any appropriate material, such as, for example, porous polyethylene.

The container 82 and the connector 88 may likewise be made of any appropriate material, and may be the same as or different from one another. By way of example only, either or both may be made of high density polyethylene or similar materials. The flexible container 82 may likewise be made of any suitable material, such as, by way of example only, a polyamide-polyethylene coextruded film.

The container 82 contains a dry form of one or more of any suitable salts used for preparation of dialysis solution. By way of example only, such suitable salts include sodium bicarbonate and sodium acetate. It will be understood by those of ordinary skill in the art that, when the powdered salt is sodium bicarbonate in particular, carbon dioxide will typically be generated from the initial contact between the fluid and the bicarbonate powder. Residual air is likewise often disposed within the container 82. As explained above, in order to provide proper removal of the salt solution from the container 82, it is necessary to maintain the opening 98 into the outlet 92 of the container 82 below the surface of the fluid contained therein. It will thus be appreciated that a reduction of gases disposed within the container 82 typically provides more space for the introduction of fluid.

Returning to FIG. 2, in order to expel air from the subsystem 12, an air separation chamber 102 may be provided downstream the container 82. For the purposes of the appended claims, the term container may include either the container 82 alone, the air separation chamber 102 alone, or the container 82 and the air separation chamber 102 collectively.

The air separation chamber 102, which is fluidly connected to the container 82 by the subsystem line 103, is designed to remove both air residually disposed within the container 82 and gases precipitating out of the bicarbonate solution during operation of the subsystem 12. During operation, air rises to the top of the air separation chamber 102, while the bicarbonate solution settles to the bottom of the air separation chamber 102. In use, bicarbonate solution may be passed from the air separation chamber 102 to subsystem line 104, while gases may be passed from the air separation chamber 102 by operation of valve 106.

Turning first to the passage of bicarbonate solution from the air separation chamber 102, flow through the subsystem line 104 is controlled by operation of a valve 107. When valve 107 is in the open position and valve 106 is in the closed position, bicarbonate solution flows through subsystem line 104 to a conductivity detector in the form of a conductivity cell 111 and a temperature detector 112. While the temperature detector 112 may be of any appropriate type, in the illustrated embodiment, the temperature detector 112 is in the form of a thermister, which is a resistor wherein the resistance varies significantly with temperature. Similarly, the conductivity cell 111 may be of any appropriate design that measures the conductivity of or provides a representative reading of the bicarbonate solution leaving the air separation chamber 102. From the conductivity cell 111 and temperature detector 112, the bicarbonate pump 113 pumps the bicarbonate solution to rejoin the main line 20c at junction 58, from which the bicarbonate solution is passed to one or both of the balancing chambers 26, 28, and on to the dialyzer 11, as explained above.

During regular operation, the air separation chamber 102 separates gas from fluid in the bicarbonate solution progressing to the junction 58 for delivery to the dialyzer 11, while the air separation chamber 36 separates gas from spent fluid returning from the dialyzer 11. It will be appreciated that this elimination of the gases in the fluids flowing to and from the dialyzer 11 facilitates efficient and accurate operation of the balancing chambers 26, 28 during regular operation of the system 10.

Those of skill in the art will appreciate that the illustrated arrangement could alternately be utilized with a premixed bicarbonate solution. In this regard, with valve 107 in the closed position, a bicarbonate port 115 may be placed into a container (not illustrated) having a premixed bicarbonate solution. By opening bicarbonate valve 116, the bicarbonate pump 113 may draw the premixed bicarbonate solution into a premixed bicarbonate line 118 and line 104, and through the conductivity cell 111 and temperature detector 112, to junction 58 for delivery to the dialyzer 11. In order to inhibit the passage of foreign substances or undissolved solids through the system, a filter 120 may be provided in the premixed bicarbonate line 118.

Returning to operation utilizing the container 82, and in order to determine if and when gas has accumulated in the air separation chamber 102, an air sensor 124 may be provided on the air separation chamber 102. It will be appreciated that the air sensor 124 may be alternately disposed and may be of any appropriate design. For example, the air sensor 124 may be a two-pronged air detection probe located at the top of the air separation chamber 102 such that an electric current between the two prongs is detected when fluid fills the chamber 102 to at least the level of the prongs. Conversely, when there is air in the chamber 102, the air between the two prongs acts as an insulator and electric current does not flow. (A similar air sensor 126 may be provided on air separation chamber 36 to provide an indication of when valve 76 should be opened to allow passage of gases from air separation chamber 36 to return line 30d.)

Flow through the air separation chamber 102 is controlled by the control valve 106. If air is not detected in the air separation chamber 102, the control valve 106 is closed, and the solution proceeds through subsystem line 104, advanced by a pump 113 to rejoin the mainline 20c at junction 58. The solution is then passed on to the balance chambers 26, 28 and to the mainline 20d for delivery to the dialyzer 11, as explained above.

Conversely, if the air sensor 124 detects air in the air separation chamber 102, the control valve 106 is opened to vent gases from the air separation chamber 102 to degassing line 122. In accordance with the invention, the degassing line 122 provides a fluid connection to the hydrochamber 24 such that gases accumulated in the air separation chamber 102 are passed to the hydrochamber 24. In the illustrated embodiment, degassing line 122 is connected to the third chamber 24c of the hydrochamber 24, although it may be coupled to the fourth chamber 24d of the hydrochamber 24 via a bypass line 128 and valve 130. In use, preferably only gases are released from the separation chamber 102 through the valve 106 for very short periods of time, rather than an air/sodium bicarbonate solution combination.

The illustrated embodiment further includes a bypass line 128 in which a valve 130 is disposed. During cleaning modes of the machine, the valve 130 may be opened in order to relive pressure built up within the hydrochamber 24.

To assist in the separation of gases from the fluid, such as purified water, contained within the hydrochamber 24, the hydrochamber 24 may include a venting structure 43 or the like. Here, the third chamber 24c of the hydrochamber 24 includes the venting structure 43, although an alternate venting structure or the like may be alternately disposed. Disposed as illustrated, gases entering the third chamber 24c from the degassing line 122 may rise upward through the fluid contained within the hydrochamber 24 to the upper portion of the third chamber 24c to be vented through the venting structure 43 to a drain or the atmosphere 132.

Under normal operation, gases only are vented from the air separation chamber 102 through the degassing line 122 to the hydrochamber 24. In order to ensure that the valve 106 and air sensor 124 are operating properly, that is, in order to monitor whether any of the sodium bicarbonate solution is being vented from the air separation chamber 102 to the hydrochamber 24 through the degassing line 122, a conductivity sensor 134 may be provided between the hydrochamber 24 and the container 82. In this way, a direct conductivity number is determined for the fluid as it flows from the hydrochamber 24 to the mainline 20c or subsystem line 56.

According to the disclosed method, the measured conductivity number may be compared to a reference conductivity number for fluid that is not diluted with a sodium bicarbonate solution. If the measured conductivity number differs from the reference conductivity by greater than a given amount or percentage, or if the measured conductivity number does not fall within a predetermined reference range, then further corrective action may be taken. Further corrective action may include, by way of example, shutting down the system 10 or providing a warning light or the like that the subsystem 12, the air separation chamber 102, the valve 106, or the sensor 124 must be checked.

The conductivity sensor 134 may also be utilized to supply a measured conductivity number to the system 10 with regard the fluid conductivity, as opposed to an estimated conductivity number, which is often utilized in calculations related to operation of the dialysis systems 10. For example, such systems 10 often assume that the fluid, e.g., water, has no conductivity. The measured conductivity number provided by the conductivity sensor 134 for fluid leaving the hydrochamber 24 may be utilized in system calculations as opposed to an assumed or estimated conductivity number.

The system 10 may include one or more controllers (not illustrated), which are capable of receiving signals from and/or activating one or more of the pumps 46, 78, 113 and/or one or more of the valves 42, 52, 54, 62-70, 72, 74, 76, 80, 106, 107, 116, 130, and/or receiving input from air sensors 124, 126, and/or conductivity cell 111, temperature detector 112, conductivity sensor 134. For the purposes of this disclosure, we refer to only one controller, although it will be appreciated that multiple controllers may be provided. The controller may be of any appropriate design, such as, for example, a Microchip PIC18F6410, although an alternate arrangement may be provided.

The operation of the dialysis system 10 will be explained herein only insofar as it relates to the venting of air from the subsystem 12. In an embodiment, the controller receives input from the air sensor 124 and conductivity sensor 134, and directs the actuation/operation of the pump 46, and valves 52, 54, 106, 107. In operation, when the controller receives a signal indicating that the air sensor 124 detects air in the air separation chamber 102, the controller directs the opening of closure of valve 106 to permit flow of gases from the air separation chamber 102 through line 122 to the hydrochamber 24. It will be noted that the controller may likewise provide a signal that actuates/operates the pump 46. When air is no longer detected by the air sensor 124, or the air sensor 124 provides a signal to the controller indicating that air is no longer detected, the controller directs the closure of the valve 106, arresting flow through the line 122.

The controller may additionally receive a signal from the conductivity sensor 134, indicating the measured conductivity of the fluid flowing from the hydrochamber 24. The controller may then compare the measured conductivity to a reference figure or range. If the measured conductivity is within a given difference from the reference figure or falls within the given range, the system continues to operate. Conversely, if the measured conductivity differs from the reference figure or range, the controller may take further action. Such actions may include, for example, closing the valve 106, lighting a warning light, or shutting down the system 10, depending upon the applied programming.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. In a system for use with a dialysis apparatus, the system including a container having an inlet and at least one gas outlet having a gas outlet control valve, a hydrochamber disposed upstream of the container, a first hydraulic line, the first hydraulic line fluidly coupling the gas outlet of the container to the hydrochamber, the gas outlet control valve disposed in said first hydraulic line to provide selective gas flow through the first hydraulic line, a second hydraulic line fluidly coupling the hydrochamber to the container inlet, and an inlet control valve disposed in the second hydraulic line to selectively control flow of fluid from the hydrochamber to the container, a method for venting gases from the container, the method comprising the steps of:

opening the gas outlet control valve to vent gases from the container to the hydrochamber, the gas outlet control valve selectively fluidly coupling the gas outlet of the container directly to the hydrochamber; and closing the gas outlet control valve when at least a portion of the gases contained within the container are vented from the container to the hydrochamber.

2. The method of claim 1 wherein the container includes a separation chamber.

3. The method of claim 2 wherein the container further includes a collapsible bag.

4. The method of claim 1 wherein the container contains salt concentrate, and the method further includes a step of advancing fluid into the container to create the solution of salt concentrate and fluid.

5. The method of claim 1 further comprising a step of advancing fluid through the hydrochamber to the container inlet.

6. The method of claim 5 further including a step of determining if any solution is vented to the hydrochamber from the container.

7. The method of claim 6 wherein the step of determining if any solution is vented includes a step of determining the conductivity of fluid advanced from the hydrochamber to the container inlet.

8. The method of claim 1 further comprising a step of advancing the solution from the container to the dialysis apparatus.

9. The method of claim 1 wherein the container further includes a solution outlet and a solution outlet control valve.

10. The method of claim 1 further comprising a step of sensing whether the container includes gases.

11. The method of claim 10 further comprising the step of opening the gas outlet control valve includes opening the gas outlet control valve when the air is sensed in the container.

12. A system for use with a dialysis apparatus, the system comprising a container having an inlet and at least one gas outlet,
a hydrochamber,
a first hydraulic line, the first hydraulic line fluidly coupling the gas outlet of the container directly to the hydrochamber,
a gas outlet control valve disposed in said first hydraulic line to provide selective gas flow through the first hydraulic line,
a second hydraulic line fluidly coupling the hydrochamber to the container inlet, and
an inlet control valve disposed in the second hydraulic line to selectively control flow of fluid from the hydrochamber to the container.

13. The system of claim 12 wherein the container includes a separation chamber.

14. The system of claim 13 wherein the container further includes a collapsible bag.

15. The system of claim 12 wherein the container further includes a solution outlet and a solution outlet control valve disposed downstream the container and selectively controlling solution flow from the container to the dialysis apparatus.

16. The system of claim 12 further including a sensor disposed to sense at least one of gas or fluid in the container.

17. The system of claim 12 further including a conductivity sensor disposed to measure the conductivity of fluid in at least one of the hydrochamber or flow from the hydrochamber.

18. In a system for use with a dialysis apparatus, the system including a container having an inlet, at least one gas outlet having a gas outlet control valve, and a solution outlet control valve at a solution outlet, the system also including a hydrochamber disposed upstream of the container, a first hydraulic line, the first hydraulic line fluidly coupling the gas outlet of the container to the hydrochamber, the gas outlet control valve disposed in said first hydraulic line to provide selective gas flow through the first hydraulic line, a second hydraulic line fluidly coupling the hydrochamber to the container inlet, and an inlet control valve disposed in the second hydraulic line to selectively control flow of fluid from the hydrochamber to the container, a method for venting gases from the container, the method comprising the steps of:

opening the solution outlet control valve at the solution outlet of the container to advance the solution to the dialysis apparatus;

subsequently opening the gas outlet control valve to vent gases from the container directly to the hydrochamber, the gas outlet control valve selectively fluidly coupling the gas outlet of the container to the hydrochamber;

closing the gas outlet control valve when at least a portion of the gases contained within the container are vented from the container to the hydrochamber;

advancing fluid through the hydrochamber to the container inlet.

* * * * *